(12) United States Patent
Ayre et al.

(10) Patent No.: US 10,220,129 B2
(45) Date of Patent: Mar. 5, 2019

(54) HEART ASSIST SYSTEM AND/OR DEVICE

(71) Applicants: Thorvascular Pty Ltd, Frenchs Forest (AU); John Begg, Fitzroy Falls (AU)

(72) Inventors: Peter Ayre, Frenchs Forest (AU); John Begg, Fitzroy Falls (AU)

(73) Assignee: Thorvascular Pty Ltd, Frenchs Forest (AU)

( * ) Notice: Subject to any disclaimer, the term of this patent is extended or adjusted under 35 U.S.C. 154(b) by 0 days.

(21) Appl. No.: 14/912,159

(22) PCT Filed: Jul. 15, 2014

(86) PCT No.: PCT/AU2014/000722
§ 371 (c)(1),
(2) Date: Feb. 15, 2016

(87) PCT Pub. No.: WO2015/021493
PCT Pub. Date: Feb. 19, 2015

(65) Prior Publication Data
US 2016/0199556 A1    Jul. 14, 2016

(30) Foreign Application Priority Data
Aug. 16, 2013 (AU) ................. 2013903091

(51) Int. Cl.
*A61M 1/10* (2006.01)
*A61M 1/12* (2006.01)
(Continued)

(52) U.S. Cl.
CPC ............ *A61M 1/125* (2014.02); *A61M 1/101* (2013.01); *A61M 1/1036* (2014.02);
(Continued)

(58) Field of Classification Search
CPC ........ A61N 1/40; A61M 1/1036; A61M 1/122
See application file for complete search history.

(56) References Cited

U.S. PATENT DOCUMENTS

| | | | |
|---|---|---|---|
| 4,957,504 A | | 9/1990 | Chardack |
| 5,613,935 A | * | 3/1997 | Jarvik ................. A61M 1/1018 600/16 |

(Continued)

FOREIGN PATENT DOCUMENTS

| | | |
|---|---|---|
| WO | 2009029977 A1 | 3/2009 |
| WO | 2010042008 A1 | 4/2010 |
| WO | 2014098782 A1 | 6/2014 |

OTHER PUBLICATIONS

"International Search Report and Written Opinion of the International Searching Authority, issued in International Application No. PCT/AU2014/000722 dated Oct. 16, 2014".

*Primary Examiner* — Joseph M Dietrich
(74) *Attorney, Agent, or Firm* — Kaplan Breyer Schwarz, LLP

(57) ABSTRACT

A cardiac assist device comprising: an implantable pump having a first and second end and adapted to be mounted within a blood vessel, wherein the pump further comprises an impeller that rotates about an axis parallel to the flow of blood through the pump and wherein the impeller lateral movement is restrained between the first and second end by bearings positioned at respective first and second ends; and wherein the pump is powered by a first implanted coil and a second external coil mounted on either side of a skin barrier of a patient, wherein the first and second coils are in electrical communication to relay power across the skin barrier.

23 Claims, 15 Drawing Sheets

(51) Int. Cl.
*A61N 1/378* (2006.01)
*A61N 1/40* (2006.01)

(52) U.S. Cl.
CPC ............ *A61M 1/122* (2014.02); *A61M 1/127* (2013.01); *A61N 1/3787* (2013.01); *A61N 1/40* (2013.01); *A61M 1/1017* (2014.02); *A61M 1/1031* (2014.02); *A61M 1/1086* (2013.01); *A61M 2205/0211* (2013.01); *A61M 2205/18* (2013.01); *A61M 2205/3375* (2013.01); *A61M 2205/3538* (2013.01); *A61M 2205/3646* (2013.01)

(56) References Cited

U.S. PATENT DOCUMENTS

| | | |
|---|---|---|
| 2008/0269880 A1 | 10/2008 | Jarvik |
| 2008/0292478 A1 | 11/2008 | Baykut et al. |
| 2010/0063347 A1* | 3/2010 | Yomtov ............... A61M 1/10 600/17 |
| 2013/0123569 A1 | 5/2013 | Gross |

* cited by examiner

HEART ASSIST SYSTEM AND/OR DEVICE

FIELD OF THE INVENTION

The present invention relates to heart or cardiac assist devices or systems or blood pumping systems.

BACKGROUND OF THE INVENTION

Previously, there has been a long felt need for a cardiac or heart assist device that improves upon the currently commercially available models for these types of medical devices.

An examples of an earlier inventions in this field are Left Ventricular Assist Devices (LVADs) which were used to reduce the pumping load on the left ventricle of the heart. Often these types of devices are bulky and relatively difficult to implant within a patient. Specifically, Heartmate™ manufactured by Thoratec, Ventrassist™ manufactured by Ventracor, HVAD™ manufactured by Heartware.

An example of a previous attempt to improve the power and data communications with respect to LVADs is described within PCT Published Patent Application No. WO2008/106717. This system includes a transcutaneous energy transfer system (TETS) for powering a LVAD system which includes a left ventricular pump, implanted controller, implanted battery, and implanted TETS circuitry which comprises at least one coil). The bulk of the described centrifugal system is a significant limitation of the usefulness of the system. Additionally, the disclosed system includes non-optimal location mountings of the implanted circuitry.

Any discussion of the prior art throughout the specification should in no way be considered as an admission that such prior art is widely known or forms part of common general knowledge in the field.

Problems to be Solved

These earlier invented devices were often too large and bulky to be used for other applications including right ventricular assistance or paediatric usage. The size also greatly impacted the body types of patients that could be treated with such a device or system.

Additionally, many of the systems and devices currently available rely on old technologies to provide power and data connections and it is an aim of the present invention to improve patient comfort by reducing the overall size of the system by improvements to power and data communication with the pumping device.

Additionally, earlier invented systems and devices were relatively inefficient in terms of power usage. Systems using transcutaneous energy transfer systems usually had transfer efficiencies of lower than 10% mainly due to heat loss.

It is an object of the present invention to overcome or ameliorate at least one of the disadvantages of the prior art, or to provide a useful alternative.

SUMMARY OF THE INVENTION

Means for Solving the Problem

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention. The present invention may be industrial applicable to the field of heart or blood pumps and more specifically those pumps requiring implantation within the body of a patient.

DETAILED DESCRIPTION

Preferred embodiments of the invention will now be described with reference to the accompanying drawings and non-limiting examples.

Figure 1:
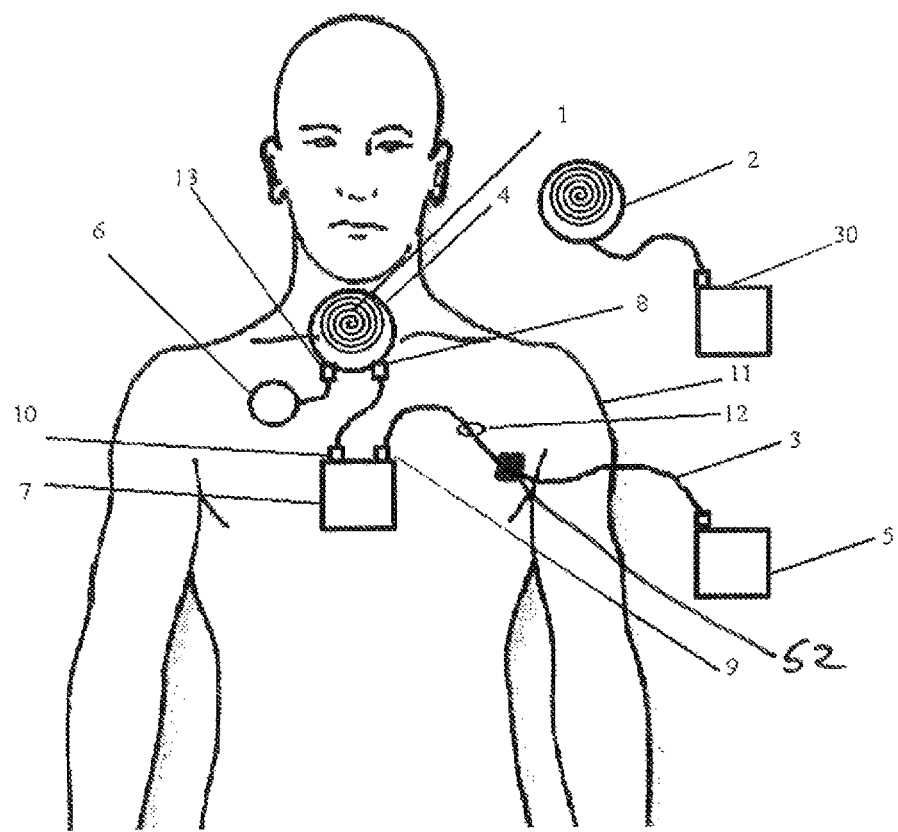
FIG. 1 is a diagrammatic representation of a first preferred embodiment of the present invention.

A first preferred embodiment of the present invention is depicted in FIG. 1, wherein a system for assisting a patient's heart, cardiac system, or blood vessel system is demonstrated.

In FIG. 1, a system or device has been implanted within a patient 11. Preferably, an implanted pump 6 is electrically connected to an implanted transcutaneous energy transfer system (TETS) 4 and that in turn is electrically connected to an implanted battery or power source 7.

In this embodiment, the battery 7 is in turn electrically connected to a percutaneous lead 3 which may be anchored to the patient 7 internally. The percutaneous lead 3 is adapted to exit the patient's 11 body through a permanent exit wound 12 and further wherein the percutaneous lead 3 may be connected to an external controller 5.

Preferably, the external controller 5 is adapted to control the charging of the battery 7 and the utilisation or pumping speed of the pump 6.

When in use, the implanted TETS housing 4 is coupled across the skin layer of the patient 11 to an external TETS housing 2. Both housings 2 include a coil of wire to enable to transmission and reception of EMF transmissions and allow for the conversion of these signals into electrical current. In this way, electrical charge may be applied to both the pump 6 and the battery 7. Additionally, data may be encrypted within the EMF transmissions to allow for the transmission of data to the external environment.

In this embodiment, the external TETS housing is electrically connected to an external power source 30.

Preferably, the first preferred embodiment is adapted to provide right ventricle support or support for paediatric patients. The pump 6 has been adapted to be a relatively small axial flow pump wherein the pump 6 may be inserted in-line with existing arteries or blood vessels of the same or similar diameter to the pump 6. Preferably, the pump is mounted or positioned in place by stitching.

In relation to the embodiment shown in FIG. 1, the placement of the implanted TETS housing 4 has been implanted high when compared to the torso of the patient thereby allowing placement of the implanted TETS housing 4 around or near to the base of the neck or at the upper extremities of the ribs. Ribs and bones may provide relatively solid and stable mounting regions for the implanted TETS housing to be mounted on whilst minimising unnecessary movement or floating of the implanted TETS housing during patient use. This greatly assists in the efficiency of the TETS link between the two TETS coils. Failure to align the coils properly may lead to significant drops in overall system efficiency.

Figure 2:
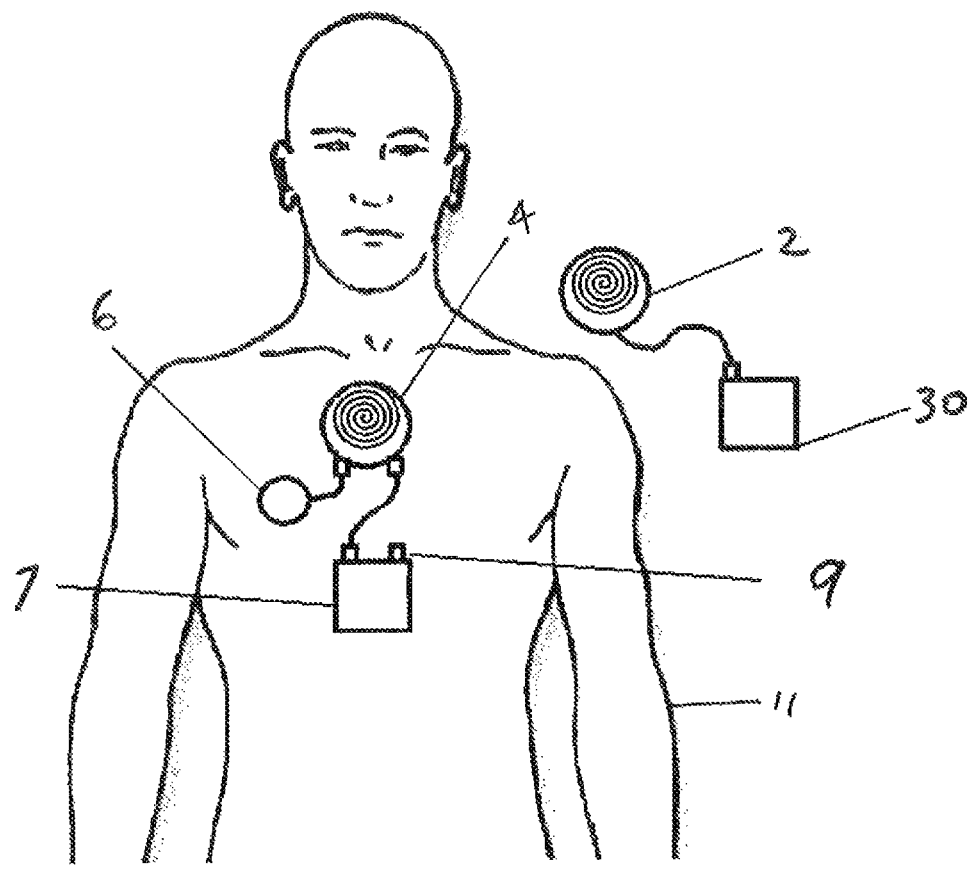
FIG. 2 is a diagrammatic representation of a second preferred embodiment of the present invention.

FIG. 2 depicts a second preferred embodiment of the present invention. In the system depicted in FIG. 2, the system has been improved by the removal of the external controller 5 and also the removal of the percutaneous lead 3. In this system, the external power source 30 is operating as the controller circuit and the system is powered and controlled only by the signals being relayed across the TETS link formed by the EMF interaction of the external TETS housing 2 and implanted TETS housing 4.

In FIGS. 1 & 2, the implanted battery 7 includes a first battery connector 9 and a second battery connector 10. In FIG. 2, the first battery connector 9 has been disconnected from the percutaneous lead 3. The system may be adapted to continue functioning even when the TETS link is disconnected as the system will revert to be powered internally by the implanted battery 7 rather than the TETS link. When the TETS link is re-established the power is switched to charging the internal battery and powered the pump from the external power source.

In the system or configuration shown in FIG. 2, the TETS housing includes a coil 1 and may also include a small control circuit that provides computation control to pump even when no external controller is connected via the TETS link. This small computational control may operate the pump 6 at a steady speed as per the last known received instruction of the external controller.

Figure 4:
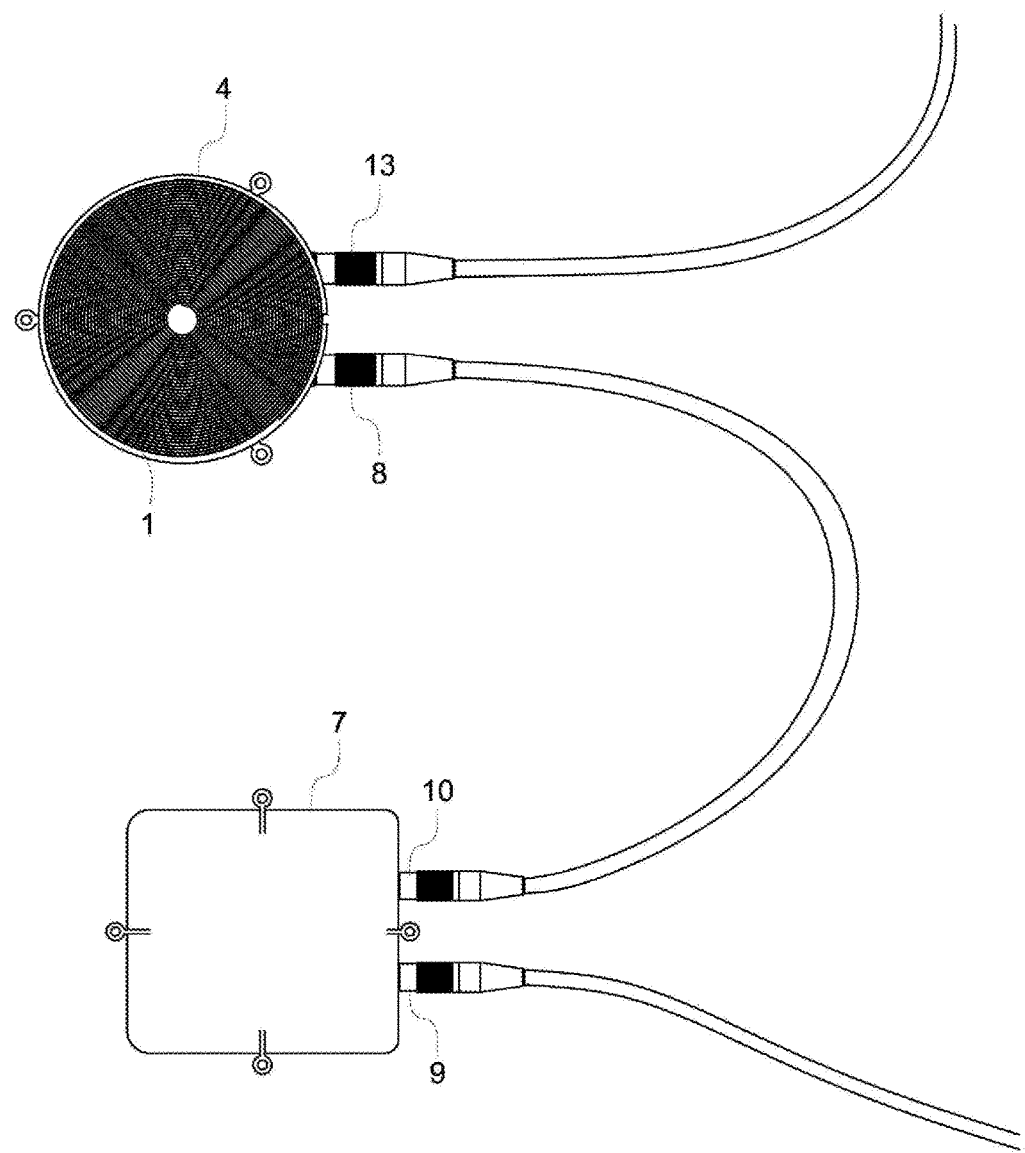
FIG. 4 depicts a top view of a portion of the implanted system or device as per the second preferred embodiment of the present invention.

FIG. 4 shows a more detailed view of the some of the implanted components forming the system depicted in FIG. 2. Preferably, the implanted primary TETS coil is shown wherein the diameter of the TETS coil is between 50-100 m with a preferred thickness of no greater than 5 mm. The preferred housing of the implanted controller shown in FIG. 4 is a general square shape when viewed from the top having sides of between 50-100 mm and a thickness of about 10-20 mm.

Figure 3:
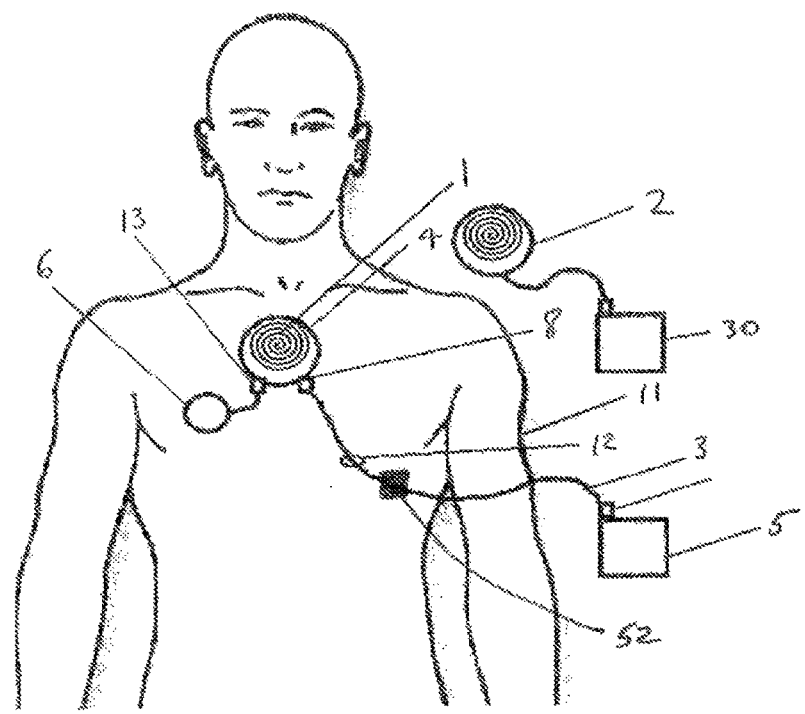
FIG. 3 is a diagrammatic representation of a third preferred embodiment of the present invention.

FIG. 3 depicts a third preferred embodiment of the present invention wherein the implanted battery has been removed from the system and replaced with external controller 5 having an integrated battery or power source.

In regard to FIG. 3, the first TETS connector 8 has been attached to the percutaneous lead 3. The second TETS connector 13 remains connected to the pump 6.

In all of the aforementioned embodiments and configurations, the connectors are adapted to be relatively water resistant or water proof to prevent fluid ingress within implanted. The connectors are preferably adapted so to allow interconnection between the connectors. Additionally, the connectors should be corrosion resistant or made of a suitable material such as titanium alloy or stainless steel. Preferably, Lemo™ style connectors are used for the connectors.

Figure 5:
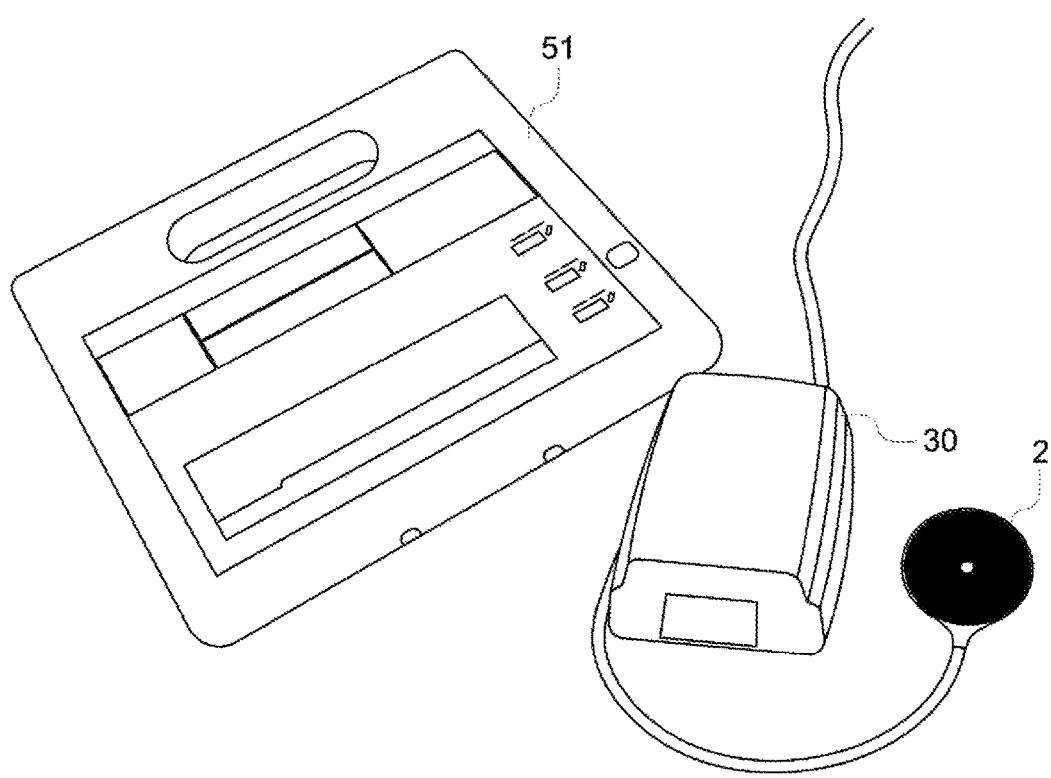
FIG. 5 depicts some of the external components that may be used with anyone of the preferred embodiments.
Figure 6:
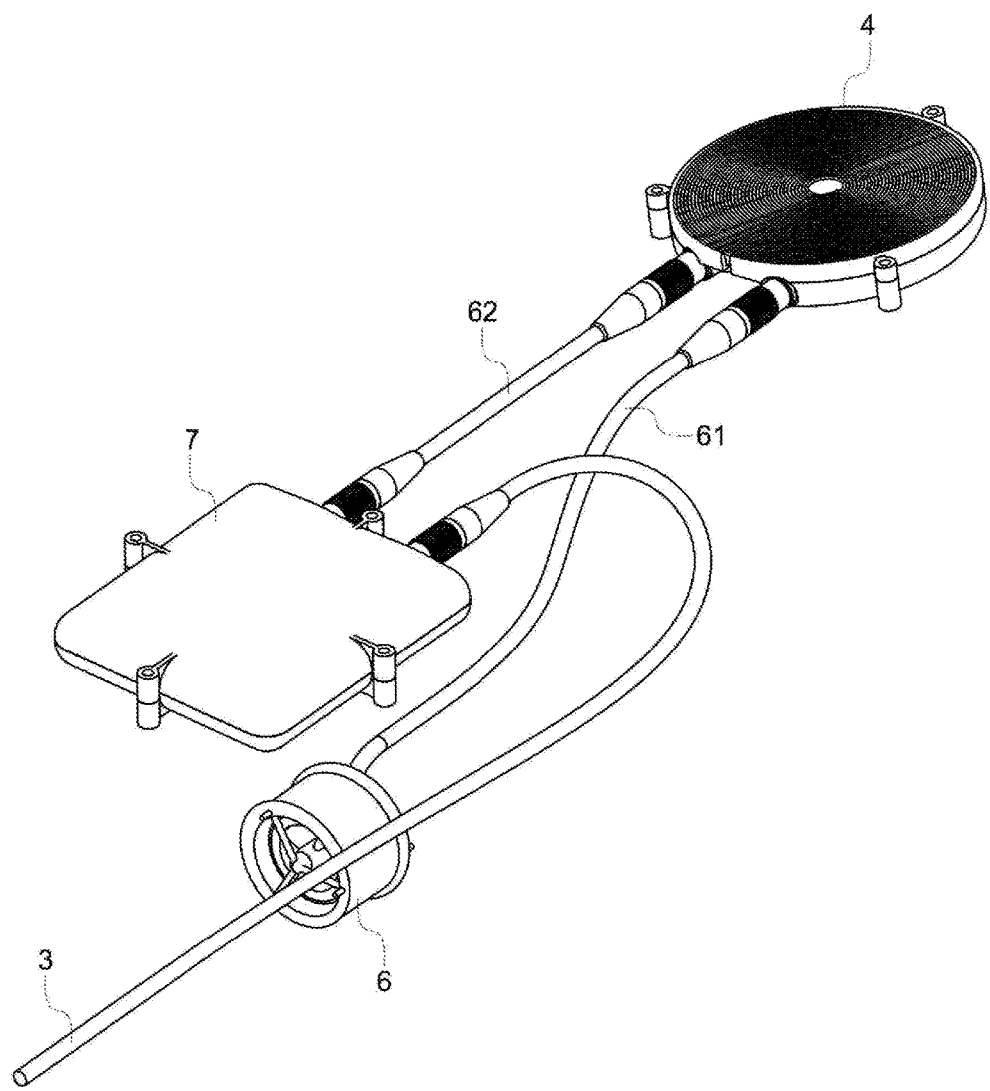
FIG. 6 depicts a more detailed perspective view of some of the implanted portions of the system or device for anyone of the preferred embodiments.

FIG. 5 depicts some of the preferred external components that may preferably used with the system or overall device. The external controller 30 may be adapted to connect to other devices such as a personal computer or tablet PC. In FIG. 5, an alternative tablet PC is shown as device 51 wherein device 51 is adapted from a regular tablet PC and uses Google Android™ as an operating system. Device 51 is adapted to shown pressure and flow rate information from the pump 6 on a graph. The information may be displayed in real time or from historical time datapoints.

Figure 7:
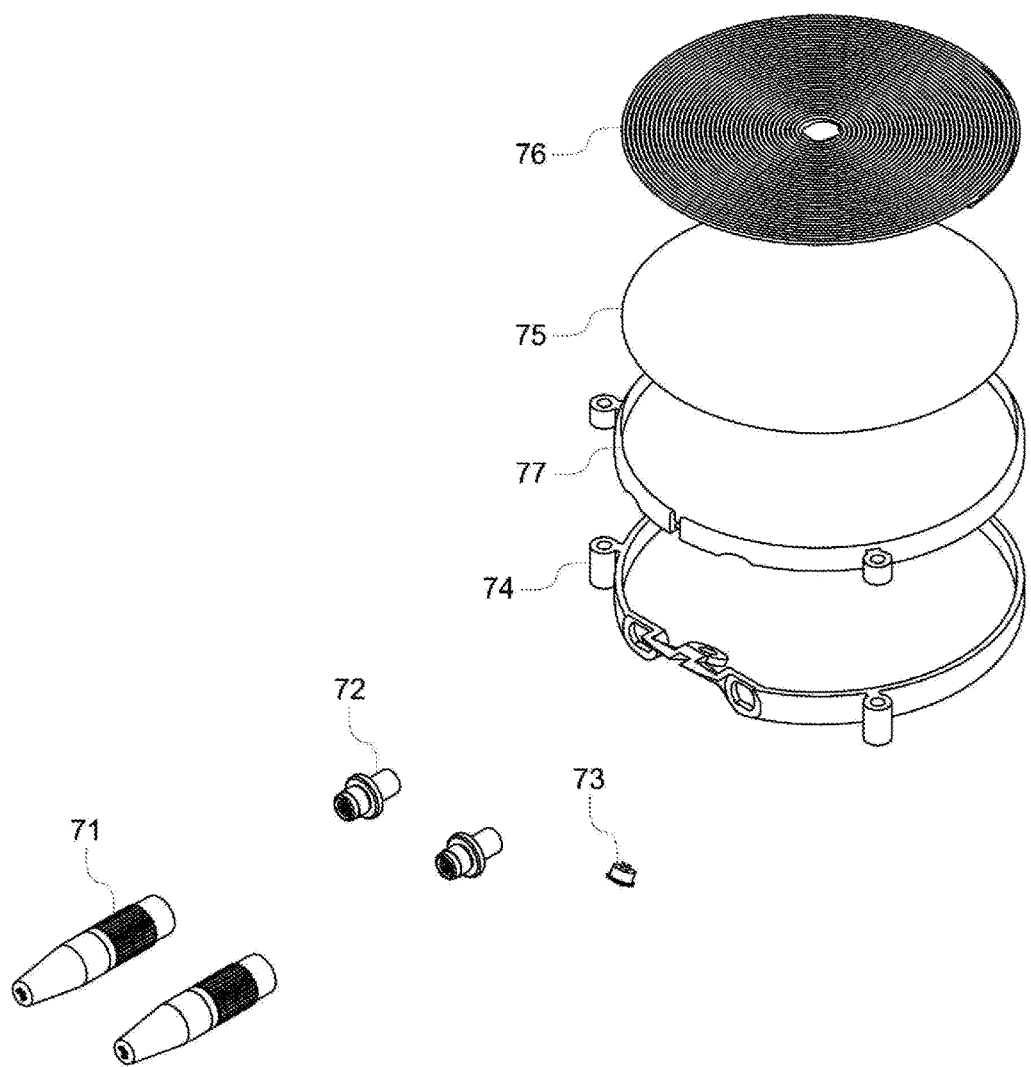
FIG. 7 depicts an exploded perspective view of the implanted TETS housing for use with any of the preferred embodiments.

FIG. 7 depicts an exploded perspective view of the TETS housings. Preferably, the TETS housings comprise the following: an upper housing portion 77 joined to a lower housing portion 74, a feed-through assembly for the wires including female Lemo™ connectors 71, male Lemo™ connectors 72 integrally joined to lower housing portion 74, a ceramic feed-through 73 to mount the wires exiting the lower housing portion 74 for joining to the male Lemo™ connectors 72; wire coil for transmission and reception of RF or EMF signals received or transmitted to the counterpart TETS housing; EMF Ferro core 75 which is generally disc shape which covers the same general surface area of the wire coil 76 which is mounted or positioned on top of core 75. Preferably, the core 75 acts to increase the electromagnetic transmission properties of the TETS link by aiding or assisting in the return of EMF waves around the TETS housing.

In FIG. 7, the upper and lower portions 74 and 77 are joined by screws mounted around the perimeter of the circular portions. However, the portions may also be joined by laser welding or gluing.

The entire TETS housing is preferably encapsulated within a silicone membrane to prevent fluid ingress or corrosion during and after implantation.

Preferably, the centre of the wire coil 76 may include a relatively small circular pad (not shown) of ceramic to form a heat sink and to move the heat generated by the operation of the TETS link away from the upper surface of the TETS housing towards the lower housing which may be constructed of a corrosion resistant metal such as titanium alloy.

Figure 8:
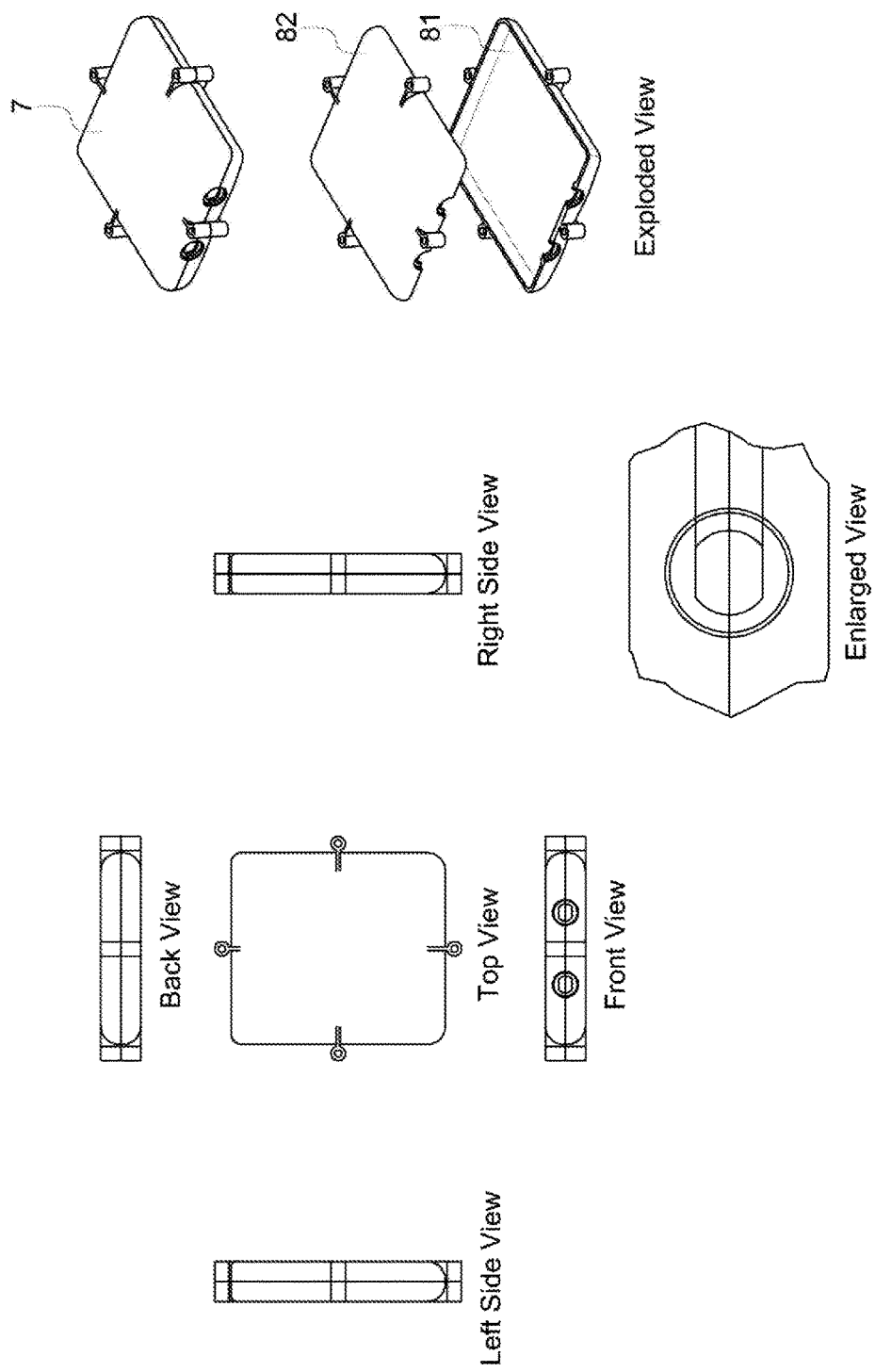
FIG. 8 depicts various views of the implanted battery for use any of the preferred embodiments.
Figure 9:
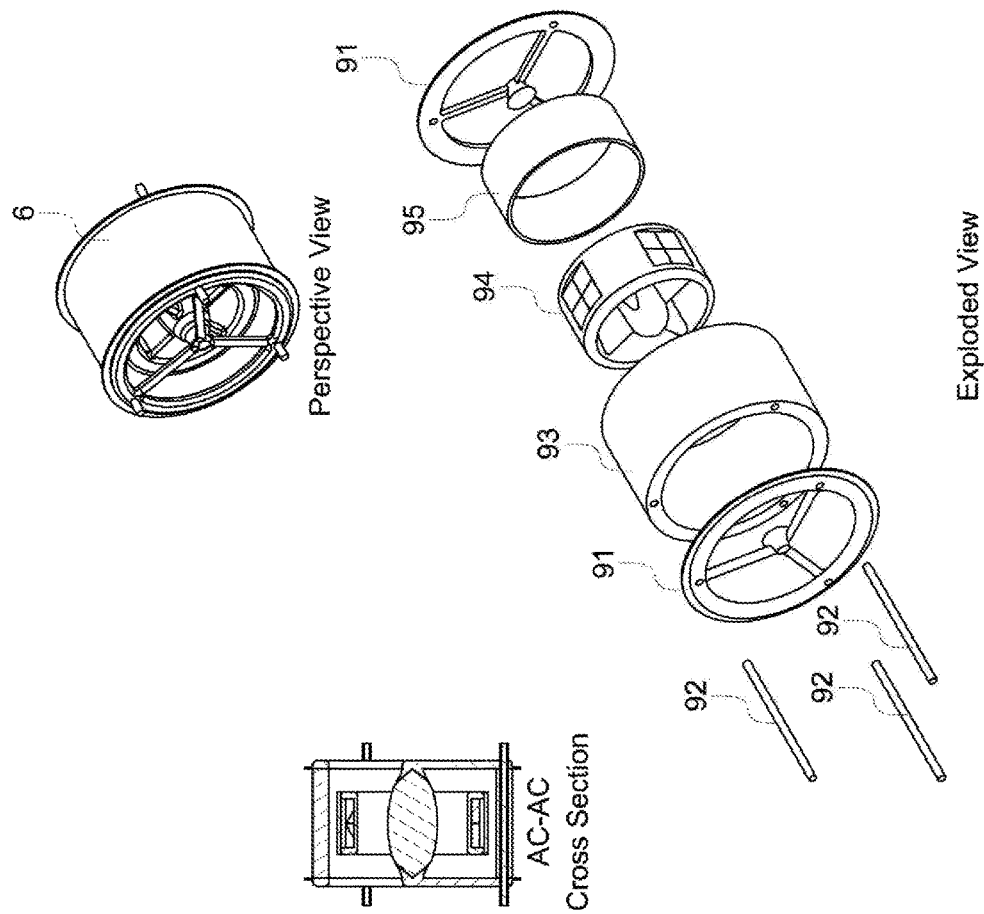
FIG. 9 depicts various views of a pump to be used with any of the preferred embodiments.
Figure 9:
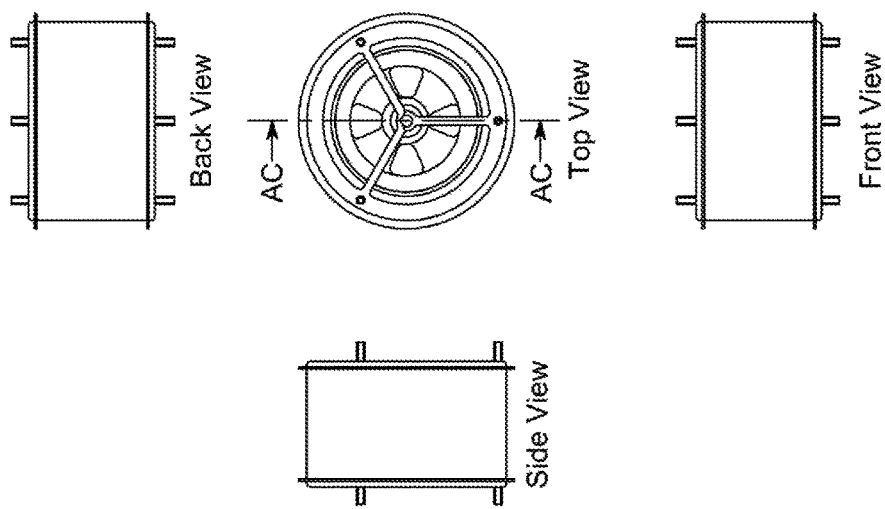
Figure 10:
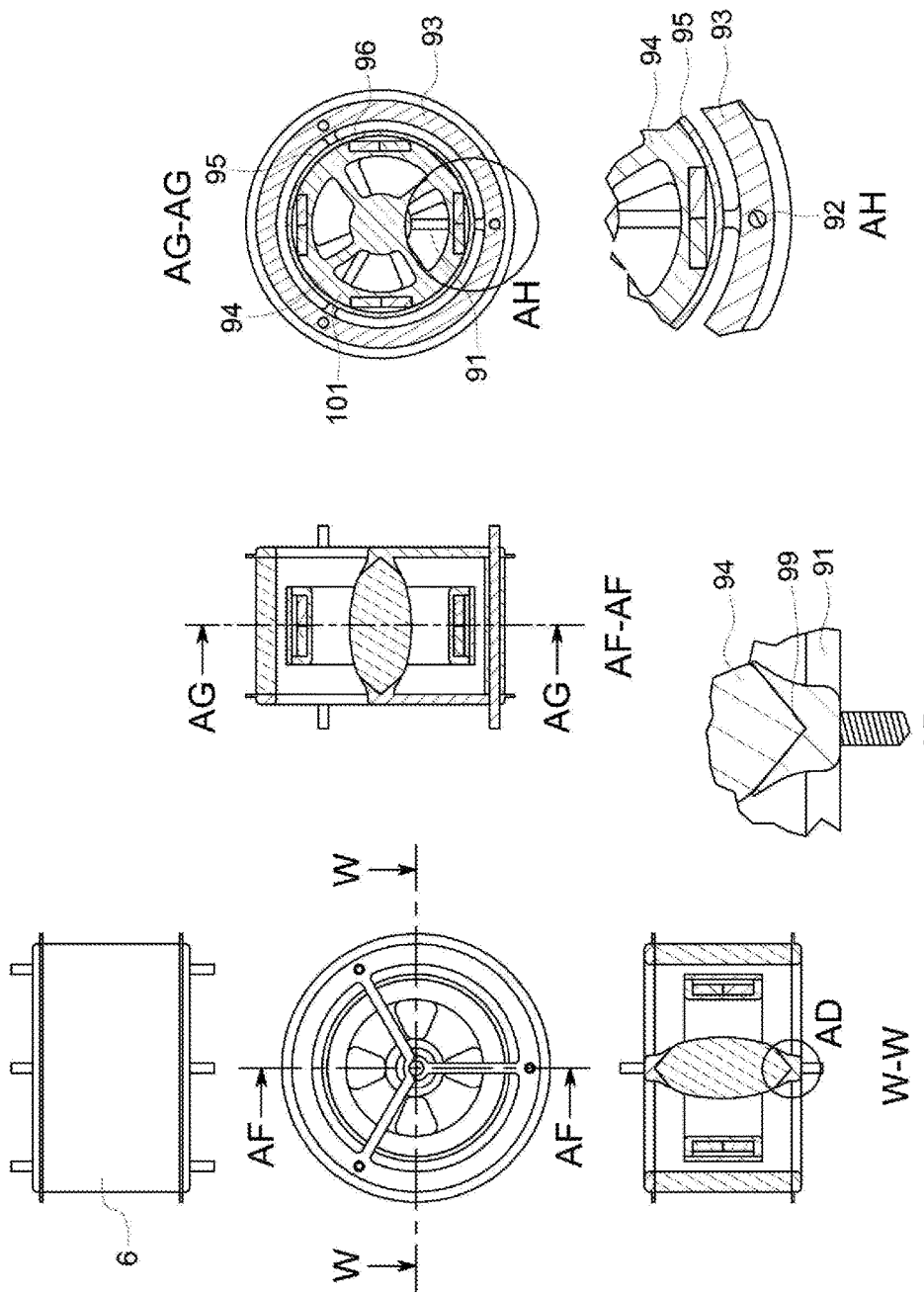
FIG. 10 depicts further detailed cross sectional views of the pump shown in FIG. 9.

FIG. 8 depicts various views of the implanted battery 7. It is noted that that the various views of the implanted battery only show the upper and lower housing portions of the implanted battery 7. The battery cells (not shown) are adapted to be encapsulated within the sealed unit formed by the joining of the upper 82 and lower 81 housing portions. The portions are preferably joined by laser welding or gluing. However in the embodiment shown in FIG. 8, the portions are joined by the mounting of screws around the perimeter of the portions. As visible from the front view, feedthroughs and connectors may be integrally joined to the internal battery 7 on the front in a similar manner to that of the TETS housing connectors.

FIGS. 9-12 depict various views of the pump 6. This pump 6 is adapted to be inserted in or in-line with an artery or blood vessel to provide blood pumping support and to reduce the pumping load on the heart or cardiac system.

The pump comprises: a rotatable impeller 94 mounted within housing 93, supports 91, pins 92, and a capping ring 95. Preferably, the pump is constructed of a biocompatible and water resistant material except for the motor components. Examples of biocompatible materials may include: PEEK, Titanium Alloy, Stainless Steel, or Polyurethane.

The impeller 94 includes a central column which is preferably cone shaped at either end. The central column is integrally joined and supports at least two blades. In this embodiment, the preferred number of blades is 4. Preferably, the blades are shorter than the central column and the central column protrudes slightly from each end of the impeller.

The blades in this embodiment are adapted to be rotated in anticlockwise direction to impart a pumping force on the blood travelling through the pump. The leading edge of the blades is preferably thicker and rounded more so than the trailing edge of the blade.

The second end of blades is integrally attached to an annular ring 95. When rotating the annular ring 95 forms a journal bearing with the inner walls of the housing 93 and assists stabilising the impeller 94 when it is rotating at high speed within the housing 93. Preferably, the gap between the outer wall of the impeller and inner wall of the housing is between 100-500 microns to give rise the hydrodynamic effect of the journal bearing to stabilise the impeller whilst rotating.

The impeller is restrained at both ends by a bearing mounted in the centre of supports 91. The supports 91 cap both ends of the housing 93 and position the impeller 94 to prevent or limit lateral movement of the impeller during operation. In operation the impeller rotates about the central column in an axis parallel to the flow of blood through the pump. This is typically termed an axial flow pump.

The bearings in the pump 6 may be preferably constructed of zirconium, ceramic or aluminium or composites thereof. Preferably, the bearings will include the smallest possible surface area that will allow them to continue to function as bearings. This feature may reduce wear and thrombogenesis.

Preferably, when in operation the impeller should be activated or rotated between 1000-25000 rpm to produce a flow output of between 1-8 L/minute.

Figure 11:
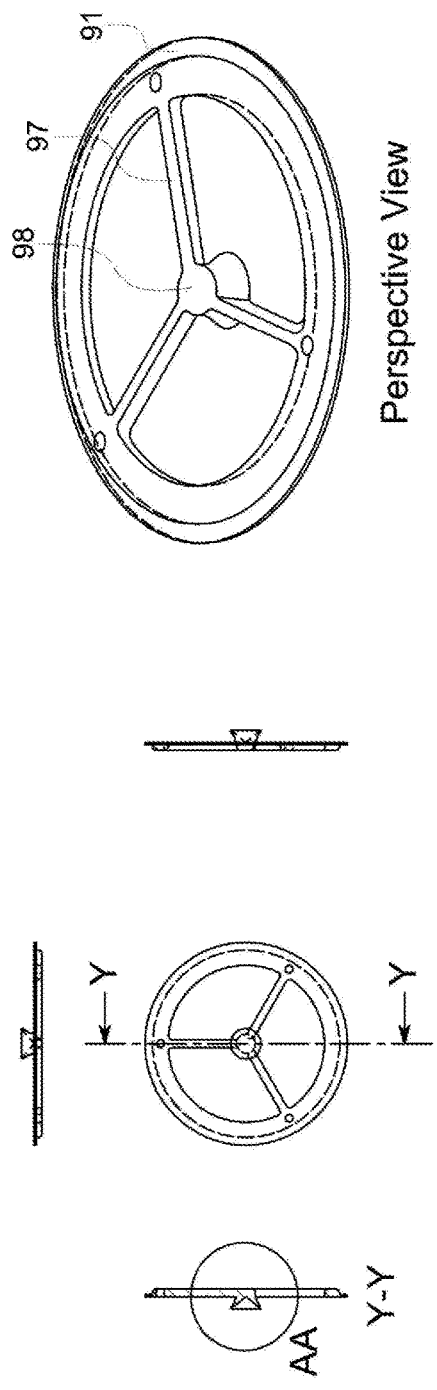
FIG. 11 depicts various views of a portion of the pump shown in FIG. 9.
Figure 12:
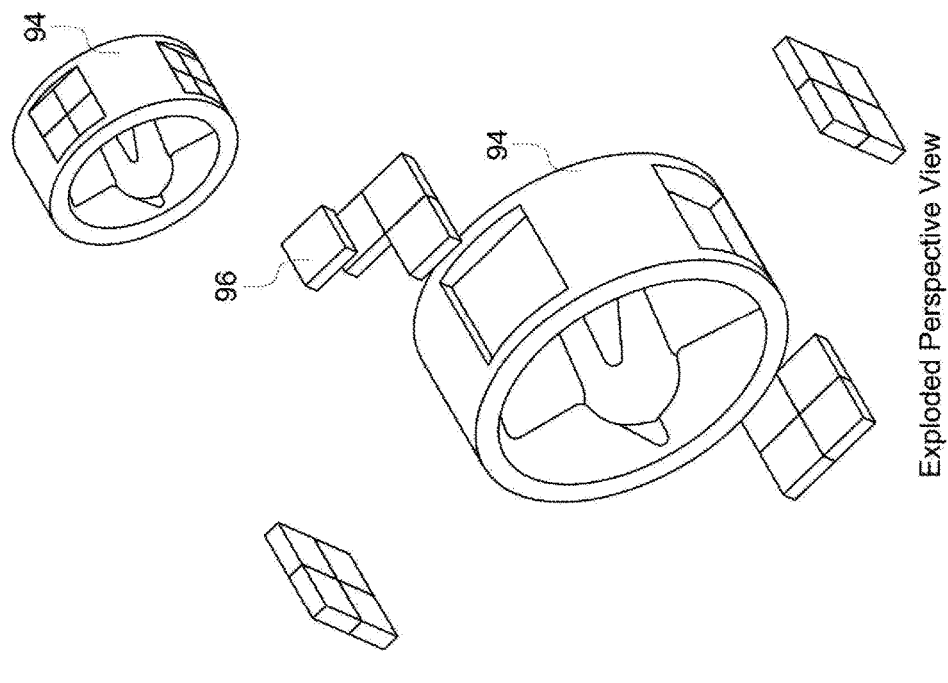
FIG. 12 depicts various views of an impeller which forms part of the pump depicted in FIG. 9.
Figure 12:
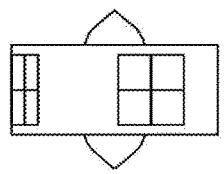
Figure 12:
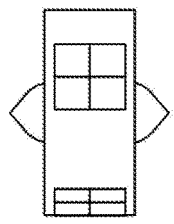
Figure 12:
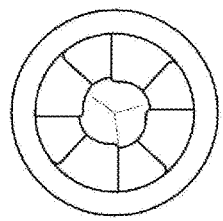
Figure 12:
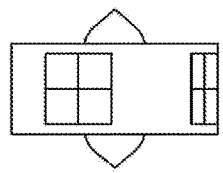

The supports 91 are shown in detail in FIG. 11, wherein the support is formed from a ring with three support spokes 97 converging at the central point 98. On one side of the central point is mounted the aforementioned cup recess 99. The spokes 97 diverge from each other at an angle of 120 degrees.

The bearing is formed in the support by a cup shaped recess adapted to receive or engage either end of the central column of the impeller. The cup recess 99 in this embodiment includes a preferred angle of 100 degrees, but other angles are possible.

The annular ring 101 of the impeller 94 includes permanent magnets 96 mounted at about 90 degree internals on the outer surface of the ring 101. The magnets 96 are constructed of rare earth magnets. The magnets are encapsulated within a capping ring 95 which seals around the annular ring 101. Preferably, the capping ring 95 is welded to the annular ring 101 to prevent or limit fluid ingress and corrosion occurring to the magnets 96. The magnets 96 are adapted to interact with motor coils mounted on the outside of the housing 93. These motor coils are not shown in the figures but are sealed around the housing 93. The electrical interaction of the coils on the magnets 96 directs the impeller 94 to rotate. The rotation of the impeller 94 imparts a pumping force on fluid within the pump (e.g. blood). Preferably, there are six motor coils mounted at equidistant points around the housing and this may form a preferred six phase motor with the interaction of the magnets located in the impeller.

Preferably, the pins 92 are inserted along lateral holes of the housing 93 and supports 91. These pins 92 engage the pump and secure the various components together when assembled. Preferably, the pins are constructed of the same of similar material to the housing and may be welded into position when inserted.

In the embodiment, shown in FIGS. 9-12 there are three pins 92 running along the length of the pump body or housing.

Preferably, the pump, device and system shown in respect of the aforementioned embodiments may be adapted to be used in applications relating to right ventricle assistance, or paediatric usage. Preferably, the pump may be shut off for small periods of time without damage to the patient, thereby negating the need for a permanent implanted battery to power to the blood pump which is commonly needed for left ventricle assist devices. Further, the axial flow configuration of the pump allows for back flow of blood through the pump during regular cardiac beating.

Preferably, the pump controller allows the pump to free wheel when no impulse is being applied to the impeller magnets, thereby allowing the pump to not significantly impede the flow of blood. Due the axial flow configuration of the pump, blood can flow through the inactive pump without being impeded.

Additionally, the embodiments of the present invention may also include Hall-effect sensors mounted in the pump housing walls to detect the flow rate or pressure of blood travelling through the pump. Alternatively, the flow rates and pressures may be calculated in a sensor-less manner using data comparing the actual energy used on the coils of pump compared to theoretical usage of energy by the coils of the pumps.

Preferably, the pump, for applications relating to right ventricle and paediatric applications, will be operated at a low power usage which is typically less than 10 W.

Further RF microphones may be mounted in or around the TETS housings to detect information relating to the quality of the TETS link. If the quality of the TETS link falls below a predetermined threshold then an alarm could be sounded. This allows the user to be instantly notified if there is a disconnection or failure of the TETS link. This failure or disconnection may occur for various reasons including: misalignment of the coils, interference of RF communications, and accidental dislodgement of external coil. Preferably, the external TETS housing may also be fitted or integrated with the aforementioned alarm.

The coils of wire used in the preferred embodiments may be constructed of Litz wire. Litz wire is generally used to make inductors and transformers, especially for high frequency application where the skin effect is more pronounced. Litz wire is often prone to material fatigue, if the material is repeatedly flexed beyond its limits. The wire is preferably coated or encapsulated with PFA, PEEK, PU or Parylene C to prevent breakage.

Figure 13:
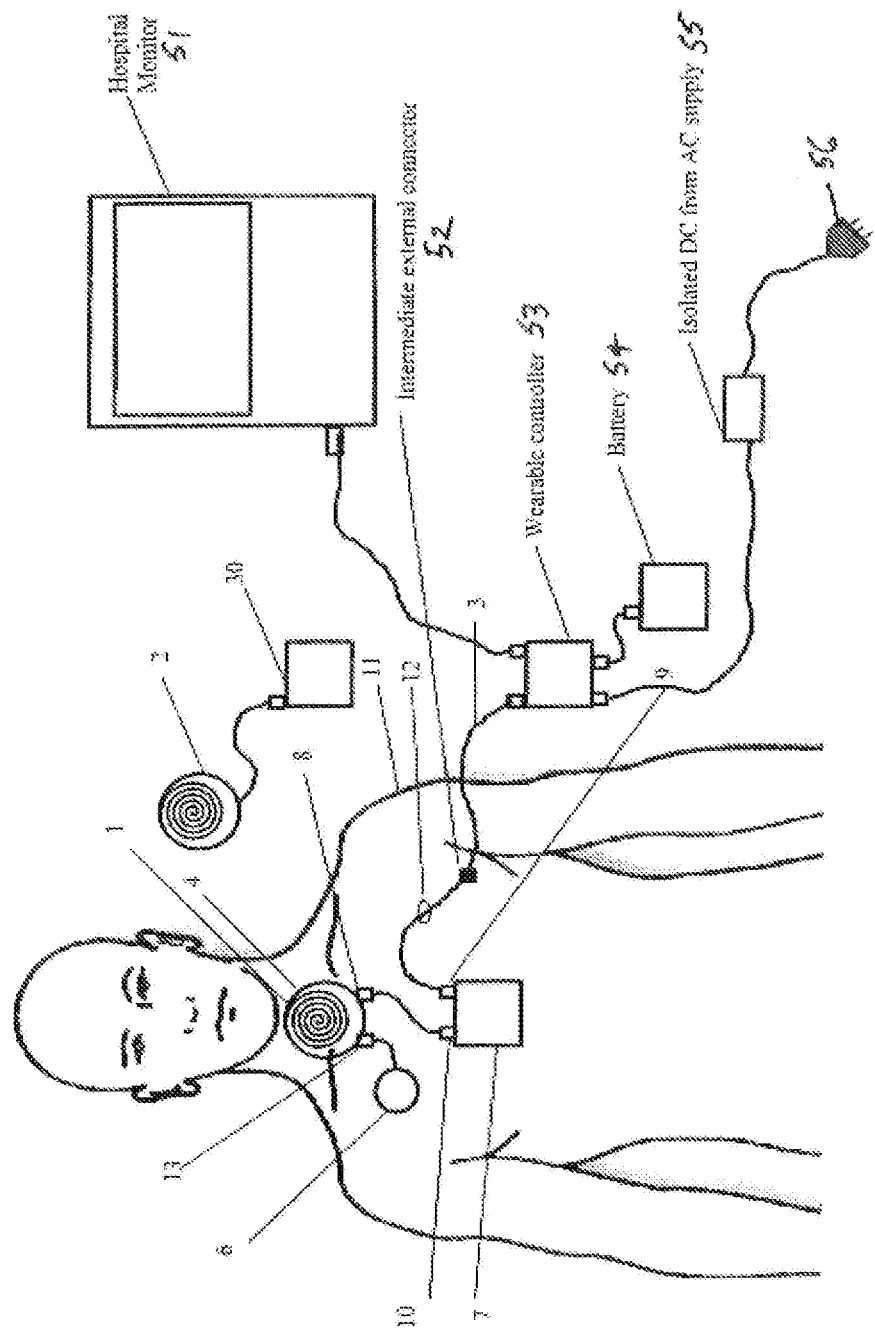
FIG. 13 is a diagrammatic representation of a further preferred embodiment of the present invention.

A further embodiment of the present invention is depicted in FIG. 13. This preferred embodiment includes an intermediate external connector 52, wherein the connector 52 is adapted to allow for the hot swapping of other systems components. Connector 52 may be optional included in any of the described embodiments. Connector 52 allows for external components to be swapped without the need for cutting and patching the percutaneous lead 3. When the connector 52 is used in conjunction with an implanted battery, the system can continue to operate without the need for an external component such as a controller or power source to be connected.

In this embodiment, a wearable controller 53 has been included and is electrically connected to battery 54. This battery 54 is preferably externally mounted relative to the patient and may be significantly larger and heavier than the implanted battery. Additionally the wearable controller 53 may be selectively connectable to a mains power or AC power connection 56 via a small AC/DC transformer 55. The wearable controller 53 may also be selectively connected to a hospital monitoring device 51.

There may be many wearable controllers connected to a single hospital monitoring device 51. This connection may be a hard wired connection or a wireless communication link (such WiFi™ or Bluetooth™).

Figure 14:
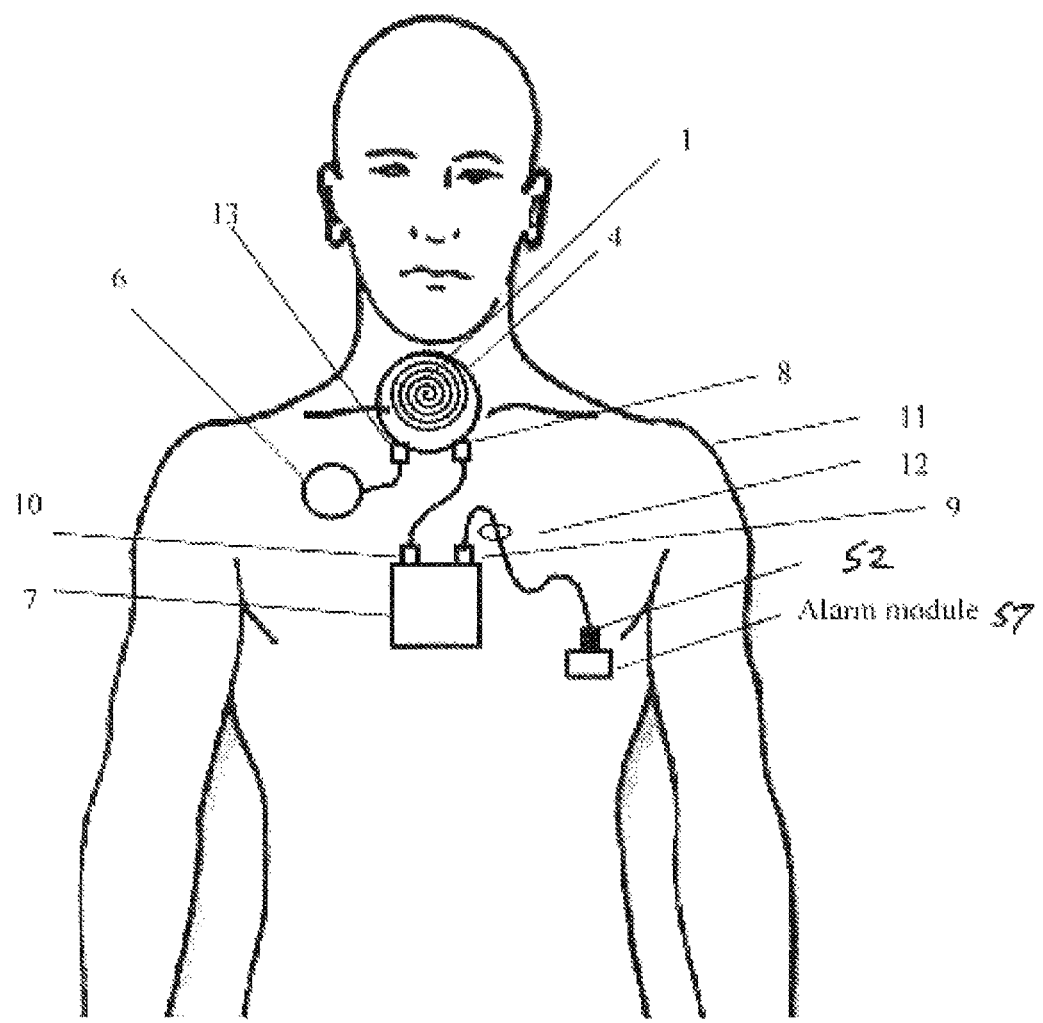
FIG. 14 is a diagrammatic representation of a further preferred embodiment of the present invention.

A further embodiment of the present invention is depicted in FIG. 14, wherein the external wearable controller 53 has been replaced with an alarm module 57. The alarm module 57 may be a small portable device adapted to be light and carried by the patient. The alarm module 57 may be electrically connected to the connector 52. Alternately, the connector 52 may be integrated into the design and housing of the alarm module 57. The alarm module 57 may be adapted to sound an audible alarm and/or may include a visual alarm. The alarm module 57 may be instructed to operate an alarm by the implanted controller or implanted pump wherein a device or system fail is noticed by the system. Also further alarms may be operated wherein the system requires maintenance or user assistance. The alarm module may also activate a vibration alarm wherein a small motor is operating within the alarm module to allow the alarm module to vibrate. It is noted that patients are generally more aware and vibrating alarms than audible or visual alarms.

Figure 15:
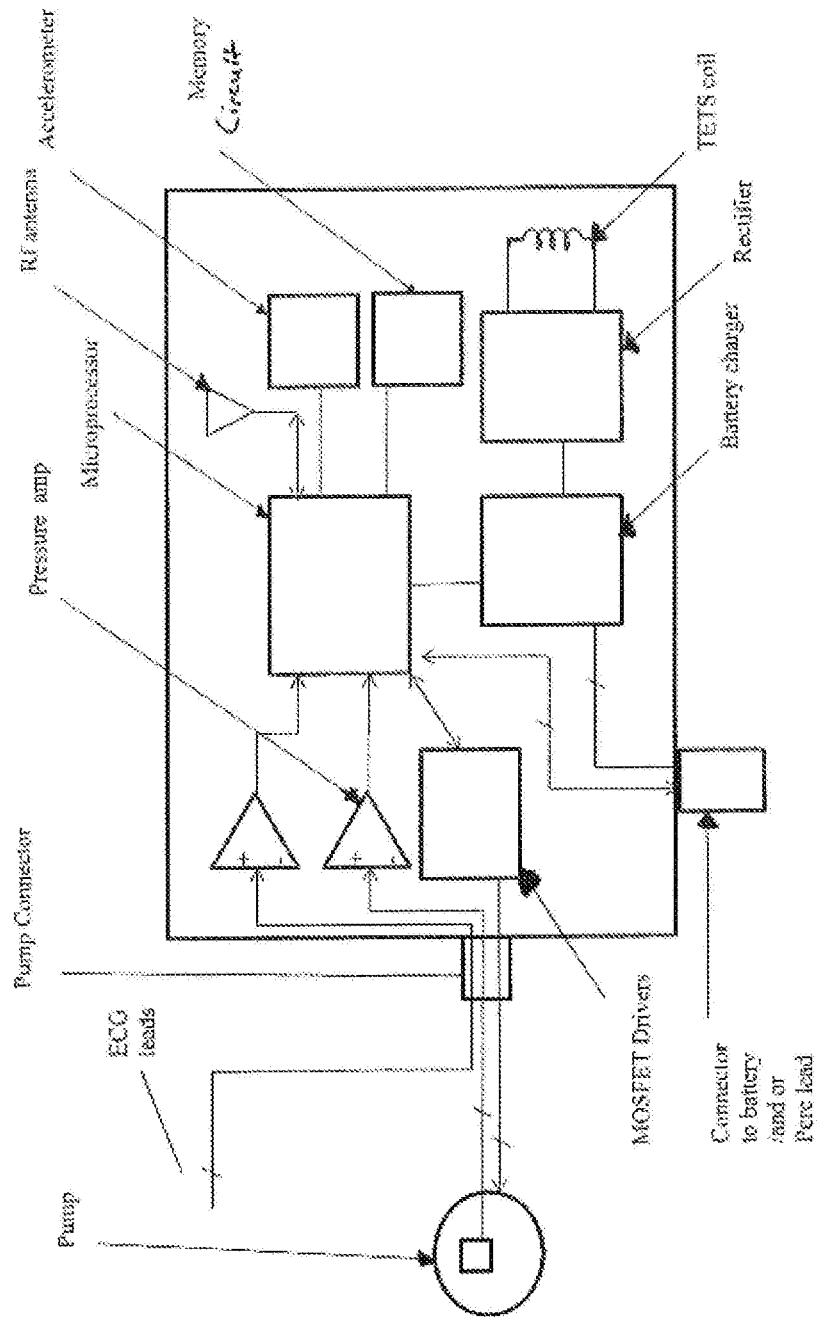
FIG. 15 is a diagrammatic representation of a preferred circuit diagram of an implanted controller to form part of a preferred embodiment.

FIG. 15 depicts a preferred circuit diagram of the module or components forming a preferred implanted controller to be used within the system or device described as one of the embodiments of the present invention. Preferably, the controller provides computation control to the implanted pump via MOSFET drivers acting under the instructions of the central processing unit or microprocessor.

The microprocessor preferably receives feedback information from sensor located or positioned within the pump. The sensor signals are feed into comparators labelled "pressure amp". The comparators generate a signal input to the microprocessor which may closely simulate the pressure waveform being experienced by the patient's blood proximal or within the pump.

The controller includes an RF antenna connected to the microprocessor for replaying signals wireless to the microprocessor.

The microprocessor is preferably connected to a memory circuit wherein the memory circuit may include RAM or FLASH memory to store data including but not limited to: the pump identifiers, time, date, pressure data, flow data, pump speed, computation speed, error logs, TETS data, and battery data.

In this embodiment, the controller includes a small battery encapsulated within the housing. The battery is adapted to maintain the pump operating as a predetermined rate even in situations wherein the external components of the system are not connected. The battery is adapted to maintain the pump operating for a relatively short period of time such as 15 minutes Preferably, the battery in the controller may be constructed on Li Ion Technology, Nickel Metal Hydride, and/or super capacitor technology.

In this embodiment, a TETS coil has been mounted within the implanted controller to reduce the overall size and space needed for the implanted system. The TETS coil is preferably connected to a rectifier which is in turn connected to the battery. The TETS coil of this embodiment is adapted to charge the battery when connected. The TETS coil integrated into the implanted controller may be hermetically sealed within the housing of the implanted controller and may also be used as a secondary TETS system. Preferably, another implanted TETS coil 2 may be used as the primary connection device. However in situations wherein the primary TETS coil 2 fails or has limited efficiency the second TETS coil within the implanted controller may be used. Thereby alleviating situations of operation disruption.

Additionally, the implanted controller of FIG. 15 may also include a 3 axis accelerometer to measure patient movement and orientation. The accelerometer may be used to detect even slight movements of the implanted controller. More preferably, the accelerometer may be used to detect the beating of patient's natural heart; or whether the patient is sleeping or the patient has fallen. In certain predetermined situations, an alarm may be activated when the accelerometer detects certain movements. Also, the pumping speed of the pump could be altered or reduced wherein the patient is at rest or sleeping.

The following information details a preferred software process for use with the preferred embodiments and may be integrated with the microprocessor of the implanted controller depicted in FIG. 15:

Implanted Controller Software Process
START IMPLANT CONTROLLER
Initialise all registers
START PUMP
READ SENSORS
CHECK CONTROL MODE
MEASURE PATIENT ACTIVITY
SEND INFORMATION and ALARMS TO WEARABLE MODULES
CHECK POWER CONNECTIONS
Goto READ SENSORS
START PUMP
   Start the pump and run at the programmed target speed for startup if the pump has stopped GOTO PUMP STOPPED
   EXIT
READ SENSORS
   Read pump inlet pressure, flow, pump speed, pump power, implanted battery status and accelerometer. Real-time clock Exit
CHECK CONTROL MODE
   If the control mode is PRESSURE Mode goto PRESSURE CONTROL. If not goto SPEED CONTROL, the mode is SPEED control mode.
PRESSURE CONTROL MODE
   Adjust the target speed so that the Target inlet pressure is reached.

If the target pressure can't be reached without the speed going beyond the programmed. speed limits GOTO SPEED CONTROL MODE. Else EXIT

SPEED CONTROL MODE

Adjust the pump speed so that the pump runs at the target pump speed.

If the target speed can not be reached, send Alarm Pump B to alarm module or wearable controller and run at programmed safety speed. ELSE EXIT

MEASURE PATIENT ACTIVITY

IF patient lying down? SET target speed range to REST speed EXIT

IF patient exercising? SET target speed range to exercise speed. EXIT

SEND INFORMATION TO WEARABLE MODULES

Send Alarms, Pressure, Flow, Speed and Power to Wearable controller EXIT

CHECK POWER CONNECTIONS

Is implant controller connected to the wearable Controller via the percutaneous lead, if yes goto PERC LEAD CONNECTED, If No goto TETS CONNECTED?

IF PERC LEAD CONNECTED—

If IMPLANTED BATTERY CONNECTED

Make sure implanted battery charged

If WEARABLE CONTROLLER CONNECTED

Send Pump variables and Alarms to wearable controller via UART

EXIT

If ALARM MODULE CONNECTED

Remind patient when running on battery only and critically if low

EXIT

IF TETS CONNECTED—

Make sure battery connected and charged

Remind patient when running on battery only and critically if low

Send data via Medical RF EXIT

PUMP STOPPED

Send Alarm critical alarm that pump won't start or stopped

GOTO START PUMP.

Although the invention has been described with reference to specific examples, it will be appreciated by those skilled in the art that the invention may be embodied in many other forms, in keeping with the broad principles and the spirit of the invention described herein.

What is claimed is:

1. A cardiac assist device comprising:
an implantable pump having first and second ends and adapted to be mounted within a blood vessel;
the pump comprising an impeller that rotates about an axis parallel to the flow of blood through the pump;
lateral movement of the impeller is restrained between the first and second ends by bearings positioned at first and second ends, respectively;
a battery adapted to power the implantable pump;
wherein when the battery is not powering the pump, the pump is powered by a first implantable coil and a second external coil mounted on either side of a skin barrier of a patient, wherein the first and second coils are in electrical communication to relay power across the skin barrier; and
wherein a ceramic heat sink positioned in the centre of the first implanted coil.

2. The device of claim 1, wherein the device is powered by only the electrical signals transmitted and received by the first and second coils.

3. The device of claim 2, wherein the device is adapted to not include a percutaneous lead nor an implanted battery.

4. The device of claim 2, wherein the pump is adapted to allow the impeller to free wheel when no electrical current is applied to the pump.

5. The device of claim 1, wherein the pump comprises a journal bearing formed between the outer surface of the impeller and inner walls of a housing, when in use.

6. The device of claim 1, wherein data is relayed between the first and second coils.

7. The device of claim 1, wherein a second heat sink is positioned in the centre of the second external coil.

8. The device of claim 1, wherein proximal to the first or second coil are mounted at least one RF microphone adapted to detect changes in quality or efficiency of the electrical communication between the first and second coil.

9. The device of claim 1, wherein an alarm is mounted proximal to the second coil and is adapted to be activated if the electrical communication falls below a predetermined threshold value.

10. The device of claim 1, wherein bearings are formed by an end of the impeller being engaged by a cup shaped recess.

11. The device of claim 1, wherein the cup shaped recess is constructed of ceramic or zirconium.

12. A cardiac assist system comprising:
an implantable pump having first and second ends and adapted to be mounted within a blood vessel;
the pump further comprises an impeller that rotates about an axis parallel to the flow of blood through the pump;
wherein lateral movement of the impeller is restrained between the first and second ends by bearings positioned at the first and second ends, respectively;
wherein the pump is powered by battery; and
wherein when the battery is disconnected from the pump, the pump can be powered by a first implanted coil and a second external coil mounted on either side of a skin barrier of a patient;
wherein the first and second coils are in electrical communication to relay power across the skin barrier; and
wherein a ceramic heat sink positioned in the centre of the first implanted coil.

13. The system of claim 12, wherein the system is powered by only the electrical signals transmitted and received by the first and second coils.

14. The system of claim 12, wherein the system is adapted to not include a percutaneous lead nor implanted battery.

15. The system of claim 12, wherein the pump is adapted to allow the impeller to free wheel when no electrical current is applied to the pump.

16. The system of claim 12, wherein the pump comprises a journal bearing formed between the outer surface of the impeller and inner walls of a housing, when in use.

17. The system of claim 12, wherein data is relayed between the first and second coils.

18. The system of claim 12, wherein a second heat sink is positioned in the centre of the second external coil.

19. The system of claim 12, wherein proximal to the first or second coil are mounted at least one RF microphone adapted to detect changes in quality or efficiency of the electrical communication between the first and second coil.

20. The system of claim 12, wherein an alarm is mounted proximal to the second coil and is adapted to be activated if the electrical communication falls below a predetermined threshold value.

21. The system of claim 12, wherein bearings are formed by an end of the impeller being engaged by a cup shaped recess.

22. The system of claim 12, wherein the cup shaped recess is constructed of ceramic or zirconium.

23. The system of claim 12, wherein the system is electrically connected to an alarm module positioned external to the patient.

* * * * *